United States Patent [19]

Desbois

[11] 4,438,043

[45] Mar. 20, 1984

[54] PROCESS FOR PREPARATION OF DI- OR TRIFLUOROMETHOXYPHENYL KETONES OR DI- OR TRIFLUOROMETHYLTHIOPHENYL KETONES

[75] Inventor: Michel Desbois, Rillieux, France

[73] Assignee: Rhone-Poulenc Specialites Chimiques, Courbevoie, France

[21] Appl. No.: 392,886

[22] Filed: Jun. 28, 1982

[30] Foreign Application Priority Data

Apr. 22, 1982 [FR] France .................. 82 6903

[51] Int. Cl.$^3$ .................. C07C 121/75; C07C 45/43; C07C 149/00
[52] U.S. Cl. .................. 260/465 F; 260/465 G; 562/426; 564/329; 568/43; 568/306; 568/319; 568/322
[58] Field of Search .................. 260/465 F, 465 G; 568/306, 319, 322, 43; 562/426; 564/329

[56] References Cited

U.S. PATENT DOCUMENTS

| | | | |
|---|---|---|---|
| T970,006 | 5/1978 | Rose | 260/591 |
| 2,273,922 | 2/1942 | Benning et al. | 260/649 |
| 2,275,312 | 3/1942 | Tinker et al. | 260/515 |
| 2,372,562 | 3/1945 | Emerson | 260/592 |
| 2,735,868 | 2/1956 | Frevel et al. | 260/592 |
| 2,781,402 | 2/1957 | Chadwick | 260/607 |
| 2,974,172 | 3/1961 | Luvisi | 260/592 |
| 3,187,057 | 6/1965 | Peter et al. | 260/651 |
| 3,387,035 | 6/1968 | Gray et al. | 260/591 |
| 3,732,307 | 5/1973 | Middleton | 260/566 B |
| 3,883,594 | 5/1975 | Schmerling | 260/592 |
| 3,953,400 | 4/1976 | Dahl | 260/47 |
| 3,967,949 | 7/1976 | Benefiel et al. | 568/322 X |
| 4,178,460 | 12/1969 | Berkelhammer et al. | 562/426 |
| 4,207,266 | 6/1980 | Opie | 260/651 F |
| 4,276,226 | 6/1981 | Clement et al. | 260/410.5 |

FOREIGN PATENT DOCUMENTS

| | | |
|---|---|---|
| 43861 | 1/1982 | European Pat. Off. . |
| 876690 | 5/1953 | Fed. Rep. of Germany . |
| 1645153 | 10/1970 | Fed. Rep. of Germany . |
| 2451037 | 4/1976 | Fed. Rep. of Germany . |
| 1567806 | 4/1969 | France . |
| 7721091 | 7/1977 | France . |
| 54-135756 | 10/1979 | Japan . |
| 1164817 | 9/1969 | United Kingdom . |
| 2030158 | 4/1980 | United Kingdom . |
| 2045760 | 11/1980 | United Kingdom . |

OTHER PUBLICATIONS

Buu-Hoi, et al., *J. Org. Chem.*, vol. 26, pp. 2401–2402, (1961).
L. Yagupol'skii et al., *Chem. Abstracts*, 61:8217, (1964).
V. Boiko, et al., *Chem. Abstracts*, 87:134226h, (1977).

*Primary Examiner*—Dolph H. Torrence

[57] ABSTRACT

A process for the preparation of di- or trifluoromethoxyphenyl ketones or di- or trifluoromethylthiophenyl ketones, characterized in that, in a first stage, a di- or trihalomethoxybenzene or a di- or trihalomethylthiobenzene is reacted with a trihalomethylated aromatic or aliphatic compound in the presence of boron trifluoride in an amount such that the absolute pressure of boron trifluoride within the reaction vessel exceeds 1 bar, and in the presence of hydrofluoric acid as a solvent and in that, in a second stage, the product of the first stage is hydrolyzed. The resultant products are useful as intermediates in the synthesis of compounds having a pharmaceutical or phytosanitary (e.g., herbicidal) activity.

12 Claims, No Drawings

PROCESS FOR PREPARATION OF DI- OR TRIFLUOROMETHOXYPHENYL KETONES OR DI- OR TRIFLUOROMETHYLTHIOPHENYL KETONES

The instant invention is directed to a process for the preparation of di- or trifluoromethoxyphenyl ketones or di- or trifluoromethylthiophenyl ketones.

Various methods for the preparation of compounds of this type are already known in the art. For example, French Patent Application No. 2,272,079 describes in particular the preparation of isopropyl p-trifluoromethoxyphenyl ketone. A Grignard reagent is prepared from p-bromophenyl oxide and trifluoromethane and magnesium, which is reacted with isobutyronitrile at reflux. The product is hydrolyzed to yield the desired ketone. French Patent Application No. 2,194,422 describes a similar process.

This type of process has serious drawbacks which make it unattractive on an industrial scale. There are numerous stages and the reaction times are long. Moreover, the yields are unsatisfactory, as they only reach 30 to 40%. In addition, and this is certainly not the least important factor, the use of organomagnesium compounds and of the solvents required for use therewith is hazardous to the environment: it is necessary to take precautions in industrial production, which increases the cost of the process.

Also known are methods for the acylation of aromatic substrates (other than trifluoromethoxybenzenes or trifluoromethylthiobenzenes) in the presence of Friedel-Crafts catalysts such as $AlCl_3$ (see, for example, Olah, *Friedel-Crafts and Related Reactions* III, Part II, Interscience Publishers, p. 8 et seq. (1964)). Experiments have shown that Friedel-Crafts catalysts, such as $AlCl_3$, are inefficient when the aromatic compound bears an $OCF_3$ or $SCF_3$ group; in fact, there is even degradation of these groups. In the presence of sulfuric acid, another classic catalyst, the $OCF_3$ and $SCF_3$ groups are similarly degraded.

A new process has now been discovered which makes it possible to prepare di- or trifluoromethoxyphenyl ketones or di- or trifluoromethylthiophenyl ketones from the corresponding di- or trihalomethoxybenzenes or di- or trihalomethylthiobenzenes, which could not be achieved according to the prior art.

The instant invention is directed to a process for the preparation of di- or trifluoromethoxyphenyl ketones or di- or trifluoromethylthiophenyl ketones, characterized in that, in a first stage, a di- or trihalomethoxybenzene or a di- or trihalomethylthiobenzene is reacted with a trihalomethylated aromatic or aliphatic compound in the presence of boron trifluoride in an amount such that the absolute pressure of boron trifluoride within the reaction vessel exceeds 1 bar, and in the presence of hydrofluoric acid as a solvent, and in that, in a second stage, the resultant product is hydrolyzed.

Within the scope of this invention, the terms di- or trihalomethoxybenzene or di- or trihalomethylthiobenzene refer both to the compounds themselves and to derivatives thereof with one or a plurality of substituents on the benzene nucleus.

More particularly, the di- or trihalomethoxybenzenes or di- or trihalomethylthiobenzenes embraced by the invention have the general formula:

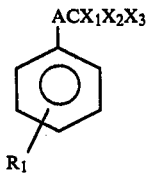

wherein $X_1$ and $X_2$ are identical or different and represent Cl, Br, I, or F; $X_3$ represents H, Cl, Br, I or F; A represents O or S; and $R_1$ represents at least one element or moiety selected from hydrogen, OH, Cl, Br, I or F alkyl and alkoxy radicals having from 1 to 6 carbon atoms and phenyl and phenoxy radicals substituted by at least one group more deactivating than the $ACX_1X_2X_3$ group.

The phenyl and phenoxy radicals $R_1$ must be substituted by groups more deactivating than the $ACX_1X_2X_3$ group so that the reaction takes place on the benzene nucleus bearing the $ACX_1X_2X_3$ group. Otherwise, the reaction would occur on the phenyl or phenoxy radical. Examples of groups more deactivating than the $ACX_1X_2X_3$ group include COOH, CN, $NO_2$, $CX_1X_2X_3$ groups and keto groups.

The compounds of Formula I in which $X_1$, $X_2$ and $X_3$ are identical are of particular interest in the present invention. Among these, compounds in which $X_1$, $X_2$ and $X_3$ represent fluorine are preferred.

One can cite as examples of compounds of Formula I the following: trifluoromethoxybenzene; trifluoromethylthiobenzene; o-, m- and p-chlorotrifluoromethoxybenzene; o-, m- and p-chlorotrifluoromethylthiobenzene; o-, m- and p-bromotrifluoromethylthiobenzene; o-, m- and p-bromotrifluoromethoxybenzene; o-, m- and p-methyltrifluoromethoxybenzene; o-, m- and p-methyltrifluoromethylthiobenzene; o-, m- and p-methoxytrifluoromethoxybenzene; o-, m- and p-methoxytrifluoromethylthiobenzene; o-, m- and p-hydroxytrifluoromethoxybenzene; o-, m- and p-hydroxytrifluoromethylthiobenzene; 4-trifluoromethyl-4'-trifluoromethoxybiphenyl; and 3-nitro-4'-trifluoromethoxydiphenyl oxide (as well as the chlorinated, brominated or iodinated analogues of the above compounds); α,α-difluoromethoxybenzene; α,α-difluoromethylthiobenzene; difluorobromomethoxybenzene; difluorobromomethylthiobenzene; dichlorofluoromethoxybenzene; dichlorofluoromethylthiobenzene; difluorochloromethoxybenzene; and difluorochloromethylthiobenzene.

Within the scope of this invention, a trihalomethylated aromatic or aliphatic compound is a compound having the formula:

$$R_2CX_4X_5X_6 \tag{II}$$

wherein $R_2$ represents an aliphatic or aromatic radical and $X_4$, $X_5$ and $X_6$ are identical or different and represent Cl, Br, or F.

The invention is well suited in particular to the use of a compound of Formula II wherein $R_2$ represents an alkyl, phenyl, alkylphenyl or phenylalkyl radical or a phenyl radical bearing at least one substituent such as, for example, halogen, $NO_2$, CN, $NH_2$ or COOH.

According to a particular embodiment of the invention, $X_4$, $X_5$ and $X_6$ are identical, and in particular, represent Cl.

Examples of compounds of Formula II include 1,1,1-trichloroethane, trichloromethylbenzene, trifluoromethylbenzene, parafluorotrichloromethylbenzene, parachlorotrifluoromethylbenzene, parachlorotrichloromethylbenzene, orthochlorotrichloromethylbenzene, metanitrotrichloromethylbenzene and 3,4-dichlorotrichloromethylbenzene.

The first stage is preferably carried out by using an amount of hydrofluoric acid such that the molar ratio of hydrofluoric acid to the di- or trihalomethoxybenzene or to the di- or trihalomethylthiobenzene is between 5 and 50. Even more preferably, this ratio is between 10 and 30.

The hydrofluoric acid used is preferably anhydrous. The use of an aqueous hydrofluoric acid would result in a useless consumption of boron trifluoride in the form of a complex of HF, $BF_3$ and $H_2O$ ($H_3O^+BF_4^-$).

The di- or trihalomethoxybenzene or di- or trihalomethylthiobenzene and the compound of Formula II are used in substantially equimolar amounts. An excess of the compound of Formula II may, however, be desirable in order to minimize the formation of polycondensation compounds.

More particularly, it is preferred to use an amount of boron trifluoride such that the initial absolute pressure of $BF_3$ within the reaction vessel is between 6 and 20 bars. The more the pressure is increased, the greater the increase in the rate of reaction. A pressure in excess of 20 bars is not excluded from the scope of the invention; however, it does not provide any particular benefit. The pressure will therefore be adjusted to maximize the efficiency of the process.

If a trichloromethylated derivative is used as the compound of Formula I or II, an increase in pressure due to the Cl-F exchange is observed.

The first stage is preferably carried out at a temperature between $-20°$ C. and $150°$ C. The reaction times are generally between a few minutes and several hours. The second stage is a hydrolysis that can be carried out in an acid or basic medium as is conventional in the art.

A practical method for carrying out the process according to the invention is to perform the hydrolysis on a raw mixture or a mixture partially freed of the HF solvent from the first stage. The reaction is therefore carried out in the presence of HF, i.e., in an acid medium. The complete removal of HF prior to the second stage makes it possible to operate in either a basic or an acid medium. The hydrolysis is preferably performed at a temperature between $0°$ and $80°$ C.

The process according to the invention can be schematically illustrated as follows:

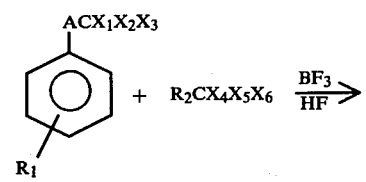

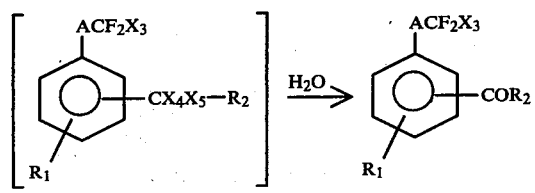

During the first stage performed in a HF medium, $ACCl_3$, $ACBr_3$, $ACI_3$, $ACF_2Br$, $ACCl_2F$, $ACF_2Cl$, etc. groups are transformed into $ACF_3$ when $X_3$ represents a halogen. When $X_3$ represents hydrogen, there is no exchange of $X_3$, and the group obtained is $ACF_2F$.

The position of the $COR_2$ group with respect to the $ACF_2X_3$ and $R_1$ groups is in conformity with the substitution rules well known to the organic chemist.

The ketones produced by the process of the invention are useful, in particular, as intermediates in the synthesis of compounds having a pharmaceutical or phytosanitary (e.g., herbicidal) activity.

The following are examples of compounds that can be prepared by the process of the invention: 4-trifluoromethoxy-2'-chlorobenzophenone; 4-trifluoromethoxy-4'-chlorobenzophenone; 4-trifluoromethoxybenzophenone; 4-trifluoromethoxyacetophenone; 4-trifluoromethoxy-4'-fluorobenzophenone; 4-trifluoromethoxy-4'-trifluoromethylbenzophenone; 4-trifluoromethoxy-2'-trifluoromethylbenzophenone; 4-trifluoromethoxy-2-chloro-4'-nitrobenzophenone; 2-trifluoromethoxy-5-methyl-4'-aminobenzophenone; 2-trifluoromethoxy-4-chloro-4'-fluorobenzophenone; 3-trifluoromethoxy-4-hydroxy-3'-cyanobenzophenone; 4-($\alpha,\alpha$-difluoromethoxy)-4'-fluorobenzophenone; 3-trifluoromethoxy-4',6-dichlorobenzophenone; and 2-trifluoromethoxy-4',5-dichlorobenzophenone, as well as the analogous trifluoromethylthio compounds.

In order to disclose more clearly the nature of the present invention, the following examples illustrating specific embodiments of the invention are given. It should be understood, however, that this is done solely by way of example and is intended neither to delineate the scope of the invention nor limit the ambit of the appended claims.

EXAMPLE 1

Into a 250 ml stainless steel reactor equipped with a magnetic stirrer system, 100 ml of anhydrous HF, 42.7 g (0.2 mole) of p-fluorotrichloromethylbenzene, and 32.4 g (0.2 mole) of trifluoromethoxybenzene were introduced at around $0°$ C. The reactor was closed and gaseous boron trifluoride introduced until the pressure was constant at 6 bars. The reaction was then allowed to proceed with stirring at ambient temperature for 3 hours. Following reaction, the reactor was decompressed to atmospheric pressure, then the reaction mixture poured over 200 g of crushed ice. Following warming up to ambient temperature, the resultant heterogeneous mixture was stirred for one to two hours, then extracted three times with 200 ml of methylene chloride. The organic phases were washed three times with 200 ml of water, once with 200 ml of a 3% aqueous potassium hydroxide solution, and twice with 200 ml of water. The organic phase was dried over magnesium sulfate and the solvent eliminated by distillation under reduced pressure. 51.9 g (yield: 76.6%) of crude 4-trifluoromethoxy-4'-fluorobenzophenone was recovered.

EXAMPLE 2

The process was carried out as in Example 1 with the following compounds and under the following conditions:
Anhydrous hydrofluoric acid: 100 g
1,1,1-trichloroethane: 40.5 g (0.3 mole)
Trifluoromethoxybenzene: 16.2 g (0.1 mole)
Boron trifluoride: 6 bars at 20° C.
Temperature: 10° C.
Duration: 5 hours 16 g (yield: 78.4%) of crude p-trifluoromethoxyacetophenone was recovered.

EXAMPLE 3

The process was carried out as in Example 1 with the following compounds and under the following conditions:
Anhydrous hydrofluoric acid: 100 g
p-chlorotrichloromethylbenzene: 46 g (0.2 mole)
Trichloromethoxybenzene: 42.3 g (0.2 mole)
Boron trifluoride: 6 bars at 20° C.
Temperature: 95° C.
Duration: 5 hours 47.6 g (yield: 67%) of crude 4-trifluoromethoxy-4'-chlorobenzophenone was recovered.

EXAMPLE 4

The process was carried out as in Example 1 with the following compounds and under the following conditions:
Anhydrous hydrofluoric acid: 100 g
Trichloromethylbenzene: 19.6 g (0.1 mole)
Trifluoromethoxybenzene: 16.2 g (0.1 mole)
Boron trifluoride: 6 bars at 20° C.
Temperature: 40° C.
Duration: 4 hours 26 g (yield: 97.7%) of crude 4-trifluoromethoxybenzophenone was recovered.

EXAMPLE 5

The process was carried out as in Example 1 with the following compounds and under the following conditions:
Anhydrous hydrofluoric acid: 100 g
Trichloromethylbenzene: 29.3 g (0.15 mole)
Difluorobromomethoxybenzene: 33.5 g (0.15 mole)
Boron trifluoride: 8 bars at 20° C.
Temperature: 80° C.
Duration: 4 hours 28.3 g (yield: 71%) of crude 4-trifluoromethoxybenzophenone was recovered.

EXAMPLE 6

The reaction was carried out as in Example 1 with the following compounds and under the following conditions:
Anhydrous hydrofluoric acid: 100 g
p-chlorotrichloromethylbenzene: 46 g (0.2 mole)
Trifluoromethylthiobenzene: 35.6 g (0.2 mole)
Boron trifluoride: 10 bars at 20° C.
Temperature: 40° C.
Duration: 8 hours 42.7 g (yield: 67.5%) of crude 4-trifluoromethylthio-4'-chlorobenzophenone was recovered.

EXAMPLE 7

The reaction was carried out as in Example 1 with the following compounds and under the following conditions:
Anhydrous hydrofluoric acid: 100 g
p-chlorotrifluoromethoxybenzene: 19.7 g (0.1 mole)
p-chlorotrichloromethylbenzene: 23 g (0.1 mole)
Boron trifluoride: 6 bars at 20° C.
Temperature: 120° C.
Duration: 18 hours 7.4 g (yield: 22%) of a crude mixture of 3-trifluoromethoxy-4',6-dichlorobenzophenone and 2-trifluoromethoxy-4',5-dichlorobenzophenone was recovered.

EXAMPLE 8

The reaction was carried out as in Example 1 with the following compounds and under the following conditions:
Anhydrous hydrofluoric acid: 100 g
α,α-difluoromethoxybenzene: 28.8 g (0.2 mole)
p-fluorotrichloromethylbenzene: 42.7 g (0.2 mole)
Boron trifluoride: 10 bars at 20° C.
Temperature: 50° C.
Duration: 3 hours 38.2 g (yield: 71%) of crude 4-difluoromethoxy4'-fluorobenzophenone was recovered.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

I claim:

1. A process for the preparation of di- or trifluoromethoxyphenyl ketones or di- or trifluoromethylthiophenyl ketones comprising reacting a di- or trihalomethoxybenzene or a di- or trihalomethylthiobenzene with a trihalomethylated aromatic or aliphatic compound in the presence of boron trifluoride in an amount such that the absolute pressure of boron trifluoride within the reaction vessel exceeds 1 bar and in the presence of hydrofluoric acid as a solvent; and hydrolyzing the resultant product.

2. A process according to claim 1, wherein the di- or trihalomethoxybenzene or di- or trihalomethylthiobenzene has the general formula:

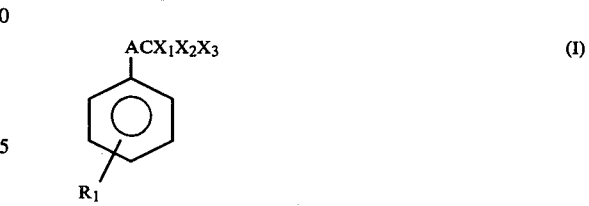

(I)

wherein $X_1$ and $X_2$ are identical or different and represent Cl, Br, I or F; $X_3$ represents H, Cl, Br, I or F; A represents O or S; and $R_1$ represents at least one element or moiety selected from the group consisting of hydrogen, OH, Cl, Br, I, F, alkyl and alkoxy radicals having 1 to 6 carbon atoms and phenyl and phenoxy radicals substituted by at least one group more deactivating than the $ACX_1X_2X_3$ group.

3. A process according to claim 2, wherein $X_1$, $X_2$ and $X_3$ are identical.

4. A process according to claim 3, wherein $X_1$, $X_2$ and $X_3$ represent fluorine.

5. A process according to claim 1, wherein the trihalomethylated aromatic or aliphatic compound has the general formula:

$$R_2CX_4X_5X_6 \qquad (II)$$

wherein $R_2$ represents an aliphatic or aromatic radical and where $X_4$, $X_5$ and $X_6$ are identical or different and represent Cl, Br or F.

6. A process according to claim 5, wherein $R_2$ represents an alkyl, phenyl, alkylphenyl or phenylalkyl radical or a phenyl radical bearing at least one halogen, $NO_2$, CN, $NH_2$ or COOH substituent.

7. A process according to claim 1, wherein an amount of hydrofluoric acid is used such that the molar ratio of hydrofluoric acid to the di- or trihalomethoxybenzene or di- or trihalomethylthiobenzene is between 5 and 50.

8. A process according to claim 1, wherein the hydrofluoric acid used is anhydrous hydrofluoric acid.

9. A process according to claim 1, wherein the di- or trihalomethoxybenzene or di- or trihalomethylthiobenzene and the trihalomethylated aromatic or aliphatic compound are used in substantially equimolar amounts.

10. A process according to claim 1, wherein an amount of boron trifluoride is used such that the absolute pressure of $BF_3$ within the reaction vessel is between 6 and 20 bars.

11. A process according to claim 1, wherein said reacting is carried out at a temperature between $-20°$ C. and $150°$ C.

12. A process according to claim 1, wherein said hydrolyzing is carried out between $0°$ C. and $80°$ C. in an acid or basic medium.

* * * * *

UNITED STATES PATENT AND TRADEMARK OFFICE
CERTIFICATE OF CORRECTION

PATENT NO. : 4,438,043
DATED : March 20, 1984
INVENTOR(S) : Michel Desbois

It is certified that error appears in the above—identified patent and that said Letters Patent is hereby corrected as shown below:

At column 4, line 15, "$ACF_2F$" should be --$ACF_2H$--.

Signed and Sealed this

Fifth Day of March 1985

[SEAL]

Attest:

DONALD J. QUIGG

Attesting Officer     Acting Commissioner of Patents and Trademarks